United States Patent [19]
Poore

[11] Patent Number: 5,620,473
[45] Date of Patent: Apr. 15, 1997

[54] CALIBRATION SYSTEM FOR PACEMAKER-GENERATED INTRACARDIAC ELECTROGRAM

[75] Inventor: John W. Poore, South Pasadena, Calif.

[73] Assignee: Pacesetter, Inc., Sylmar, Calif.

[21] Appl. No.: 400,646

[22] Filed: Mar. 8, 1995

[51] Int. Cl.$^6$ ............................................. A61N 1/37
[52] U.S. Cl. .................... 607/27; 607/31; 607/32
[58] Field of Search ............................ 607/27, 32, 60, 607/31, 28

[56] References Cited

U.S. PATENT DOCUMENTS

| | | | |
|---|---|---|---|
| 3,756,245 | 9/1973 | Thaler et al. | 128/419 P |
| 4,088,139 | 5/1978 | Auerbach | 128/419 P |
| 4,295,474 | 10/1981 | Fischell | 128/697 |
| 4,374,382 | 2/1983 | Markowitz | 340/870 |
| 4,596,255 | 6/1986 | Snell et al. | 128/697 |
| 4,712,179 | 12/1987 | Heimer | 364/417 |
| 4,712,555 | 12/1987 | Thornander et al. | 128/419 |
| 4,788,980 | 12/1988 | Mann et al. | 128/419 |
| 4,791,936 | 12/1988 | Snell et al. | 128/697 |
| 4,809,697 | 3/1989 | Causey et al. | 128/419 |
| 4,892,102 | 1/1990 | Astrinsky | 607/27 |
| 5,123,419 | 6/1992 | Platt et al. | 607/27 |
| 5,292,341 | 3/1994 | Snell | 128/419 |
| 5,309,919 | 5/1994 | Snell et al. | 128/697 |
| 5,402,794 | 4/1995 | Wahlstrand et al. | 607/32 |
| 5,444,638 | 8/1995 | Kwong et al. | 364/413.06 |

OTHER PUBLICATIONS

Johnson et al., "A simplified approach to Electrocardiography," W. B. Saunders Co., pp. 17 & 18. 1986.

Primary Examiner—William E. Kamm
Assistant Examiner—Kennedy J. Schaetzle

[57] ABSTRACT

A calibration system for use with an implantable pacemaker allows the intracardiac electrogram (IEGM) generated by the pacemaker to be calibrated when the pacemaker is coupled to an external programmer. The calibration system includes telemetry circuits within both the pacemaker and programmer that allow data signals to be sent from the pacemaker to the programmer, and that allow command signals to be sent from the programmer to the pacemaker, in conventional manner. The system further includes circuitry within the pacemaker that generates a precision reference voltage as well as a zero reference voltage, and that selectively switches the precision reference voltage and/or the zero reference voltage into the IEGM data signals being telemetered to the external programmer from the pacemaker. The switching of the precision reference voltage and/or zero reference voltage into the IEGM data occurs within the pacemaker upon receipt of a special calibration command signal from the programmer. Such reference voltages, when thus included as part of the telemetry data received from the pacemaker, is thereafter included in the display or storage of the IEGM at the programmer, and may be used to scale the IEGM display so that it fits a calibrated n mv/div graticule. The precision reference voltage thus provides a known calibrated reference against which the IEGM can be compared in order to provide a true measure of its amplitude at any given time.

25 Claims, 5 Drawing Sheets

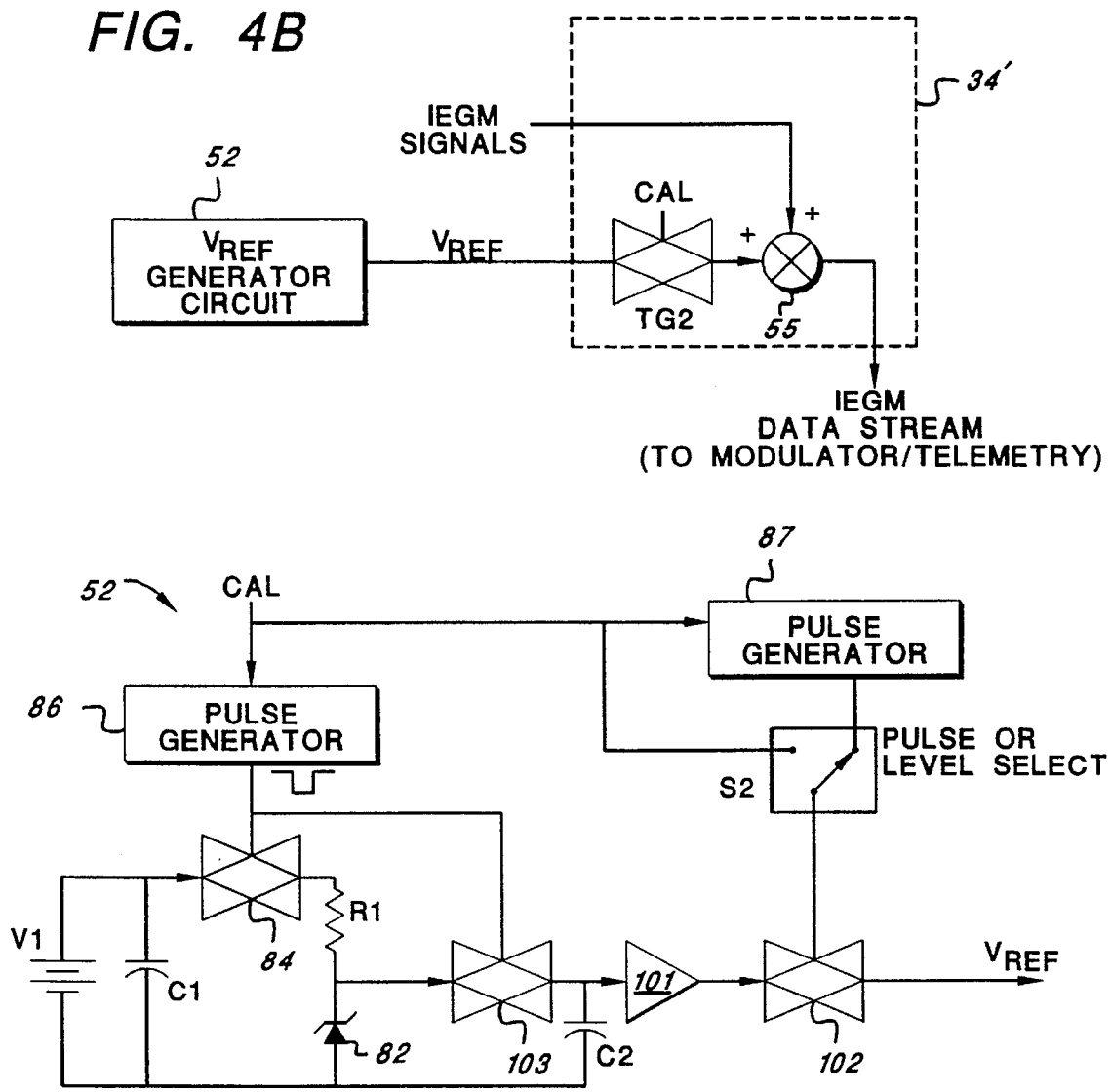
FIG. 4B
FIG. 5A
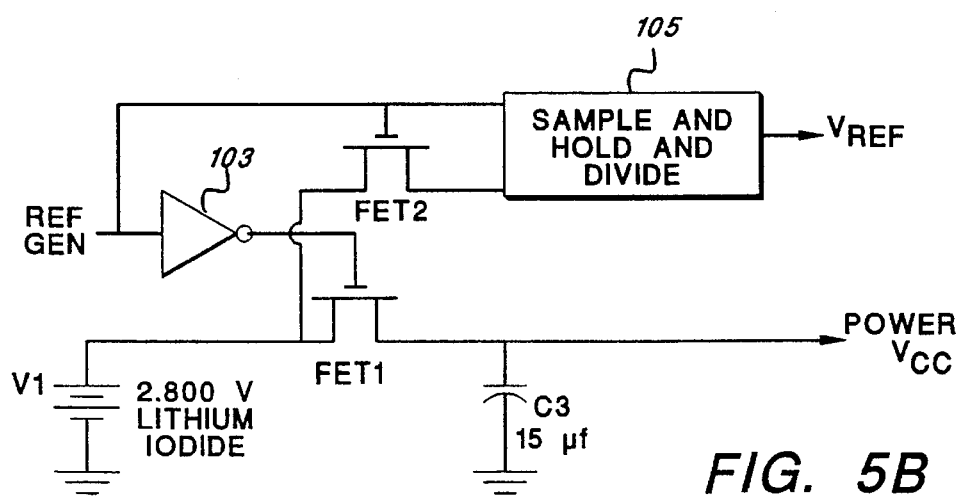
FIG. 5B

CALIBRATION SYSTEM FOR PACEMAKER-GENERATED INTRACARDIAC ELECTROGRAM

FIELD OF THE INVENTION

The present invention relates to implantable medical devices and methods, and more particularly to a pacing system that permits calibration of the intracardiac electrogram (IEGM) that is sensed by an implantable pacemaker system and telemetered to an external programmer for display, printout and/or storage.

BACKGROUND OF THE INVENTION

Modern implantable pacemaker systems (comprising an implantable pacer having leads that connect the pacer to the heart) include the ability to sense the IEGM, convert it to electrical (data) signals, and telemeter the IEGM signals to an external device (typically referred to as a "programmer"). At the external device, or programmer, the IEGM signals are processed to recreate the IEGM and display and/or print it for analysis, or store it for subsequent analysis. The IEGM thus displayed/printed or stored is comparable with, and in many ways superior to, the conventional electrocardiogram (EKG), sensed through skin electrodes.

The IEGM obtained via telemetry from an implanted pacemaker has heretofore been useful primarily to understand the relative timing between the various cardiac/pacing events manifest by it, and for comparison of relative amplitudes between various portions of the IEGM. In a dual-chamber pacemaker, i.e., one that can sense in both the atrium and the ventricle, the IEGM readily indicates the occurrence of, and timing between, either a natural or paced atrial depolarization, and either a natural or paced ventricular depolarization. The timing of such events is of critical importance to the cardiologist or physician who is analyzing the performance of the implanted pacemaker.

Unfortunately, heretofore, there has been no way to calibrate the magnitude (amplitude) of the displayed IEGM signal. That is, unlike conventional skin electrocardiographic (EKG) devices that use skin electrodes to sense cardiac activity, and which conveniently provide a "calibrate signal" that allows the physician to calibrate and verify the absolute volts per division that appear on the paper or screen trace of the EKG device, there is no such calibrate feature provided by IEGM display systems. This is because in an IEGM display system, the electrogram signals displayed originate within or on the myocardiogram of the heart, and are sensed through the pacemaker leads and appropriate sensing circuits. Because the sensed IEGM originates inside of the body, there has not heretofore been a convenient mechanism for noninvasively comparing such sensed signals to a known standard. Further, once sensed, the IEGM signals are then encoded by the implanted pacemaker, telemetrically transferred to the external programmer, and then decoded, digitized, and formatted for display on the programmer screen by the external programmer. All of this signal telemetering and processing may introduce significant variations in the amplitude of the signals thus displayed. As a result, any "calibrate" signal inserted into the display at the programmer would not take into account scale factor variations occurring in the pacemaker or in the telemetry process. As a result, the physician or cardiologist is not able to verify the "gain" of the pacemaker-programmer system from one patient visit to another, or of one patient to another (where comparative studies are desired).

The "gain" of the pacemaker-programmer system represents how much the electrical signals measured on the myocardium are amplified or attenuated as such signals are sensed by the pacemaker's sensing circuits, encoded by the implanted pacemaker, telemetrically transferred to the external programmer, and then decoded, and formatted for display on the programmer screen by the external programmer. Knowing such "gain" could be an important and useful factor when tracking the performance of the pacemaker-programmer system for a given patient, or for a group of patients. A significant change in such "gain", for example, could signal a condition that needs to be investigated either with the patient and/or the pacemaker/programmer equipment used to monitor the patient. Little or no change in such "gain" could signal that the monitoring conditions are essentially the same as existed on a prior occasion.

In order to calibrate the "gain" of the pacemaker/programmer system, it is necessary to insert a signal of known amplitude (e.g., a calibrated reference voltage) into the data stream that is being telemetered from the pacemaker to the programmer. While some prior art pacemakers have deliberately inserted a marker signal into the telemetered data in order to signal the occurrence of certain sensed events, see, e.g., U.S. Pat. No. 4,374,382, no known pacemaker generates and then selectively inserts (e.g., upon receipt of an externally-generated calibrate command signal from the programmer) a calibrated reference voltage into the telemetered data for the purpose of calibrating the amplitude of the IEGM or other data telemetered from the pacemaker.

What is needed, therefore, is a system that selectively inserts a known reference signal into the telemetry data stream in order to allow the pacemaker/programmer "gain" to be verified. The present invention advantageously addresses this and other needs.

SUMMARY OF THE INVENTION

The present invention provides a calibration system for use with an implantable pacemaker that allows the intracardiac electrogram (IEGM) generated by the pacemaker to be calibrated when the pacemaker is coupled to an external programmer. The calibration system utilizes the conventional telemetry circuits within both the pacemaker and programmer to transmit IEGM data signals from the pacemaker to the programmer, and to transmit command signals from the programmer to the pacemaker. Calibration circuitry within the pacemaker includes: (1) a voltage source that generates a precision reference voltage, and (2) a calibration switch that switches the precision reference voltage into the IEGM data stream being telemetered to the external programmer. Calibration circuitry within the programmer includes a button, or equivalent manual activation means, that when activated generates a special calibration control signal that is telemetered to the pacemaker. Upon receipt of the special calibration control signal, the pacemaker activates the calibration switch to insert the precision reference voltage into the IEGM data signals being telemetered to the programmer. When received at the programmer, the precision reference voltage is thus included in the IEGM data signals, which IEGM data signals may be displayed, printed, and/or stored. When the precision reference voltage is displayed with the IEGM data signals, a true measure of the amplitude (e.g., in millivolts) of the IEGM data signals, and hence an indication of the pacemaker/system "gain", is thus provided.

Once the pacemaker/system "gain" is known, the "gain" in the programmer can be adjusted to compensate for variations in the pacemaker's gain. Such adjustment thus allows standard graticule units of n millivolt steps to be part of the display/print of the IEGM data signals.

The calibration command can be manually invoked whenever a CALIBRATE button, included as part of the programmer (either as a separate control button, or as part of a touch-screen display of commands) is pressed or touched by the user. The calibration command may also be invoked automatically at IEGM startup, or periodically whenever IEGM data signals are being telemetered from the pacemaker to the programmer. Whenever and however invoked, the calibrate command allows for scale factor calibration. Such scale factor calibration or correction can be made temporarily in the programmer, or permanently (or "temporarily") in the pacemaker. (A "temporary" change is one that is made and used only for purposes of the current IEGM data signal transfer.)

Advantageously, using the calibration system herein described, it is possible for a physician or cardiologist (or the programmer itself) to verify the pacer/programmer system gain from one patient visit to another, or from one patient to another (where comparative studies are desired). Such verification/calibration of the IEGM data has not heretofore been available in an implanted pacemaker system. Further, by invoking automatic scale factor adjustment, the scale factor is dynamically adjusted automatically in a closed loop fashion.

The present invention may thus be characterized as an IEGM calibration system. Such system includes both an implanted pacemaker and an external programmer. The implanted pacemaker includes an implanted receiver that receives control signals from a remote transmitter located within (or coupled to) the external programmer. The pacemaker further has means for sensing intracardiac electrogram (IEGM) signals and means for telemetering such IEGM signals to a remote receiver located within (or coupled to) the external programmer. The pacemaker further includes a voltage source that generates a precision reference voltage, and a switching circuit, responsive to a calibration control signal, that inserts momentarily the precision reference voltage into a data stream (in lieu of sensed IEGM data signals) that are telemetered to the remote receiver.

The external programmer of the IEGM calibration system includes the remote receiver, the remote transmitter, processing means for processing the received IEGM signals for display, printing, and/or storage, display/print means for displaying the processed IEGM signals as a function of a selected time base, and memory means for storing the processed IEGM signals for later display/printing and/or analysis. The external programmer also includes means for generating the calibration control signal at selected times and coupling it to the implanted receiver within the pacemaker, thereby causing the precision reference voltage to be telemetered to the programmer in lieu of IEGM data signals. When such precision reference voltage is received, the processing means of the external programmer includes such reference voltage as part of the display, print, or storage of the IEGM signals. For example, the reference voltage may be displayed/printed adjacent the displayed/printed IEGM signals. Alternatively, the reference voltage may be superimposed on the display/print of the IEGM signals.

Typically, the reference voltage appears as a level or pulse. The amplitude of the reference voltage level or pulse is known. Therefore, the IEGM signals can be compared against the known amplitude of the reference voltage level or pulse for calibration purposes.

It is thus a feature of the invention to provide an IEGM calibration system that allows the system "gain" of a pacemaker/programmer system to be verified and, if desired, adjusted.

It is another feature of the invention to provide such an IEGM calibration system that generates and injects a calibrated voltage pulse or level into the IEGM data that is telemetered from an implanted pacemaker to an external programmer upon command from the external programmer.

It is a further feature of the invention to provide a pacemaker/programmer system that allows the IEGM sensed by the pacemaker to be displayed, printed, and/or stored, and wherein the absolute volts per division or graticule of such display or print may be set to conventional and familiar units—e.g., 1 millivolt (mv)/div, 2 mv/div, 5 mv/div, 10 mv/div, etc.

BRIEF DESCRIPTION OF THE DRAWINGS

The above and other aspects, features and advantages of the present invention will be more apparent from the following more particular description thereof, presented in conjunction with the following drawings wherein:

FIGS. 4A and 4B respectively show schematic block diagrams of alternate configurations of the precision reference voltage and switch used within the pacemaker;

FIGS. 5A, 5B and 5C illustrate different types of precision reference voltage circuits that may be used as the precision voltage source of FIGS. 4A and 4B.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Figure 1:
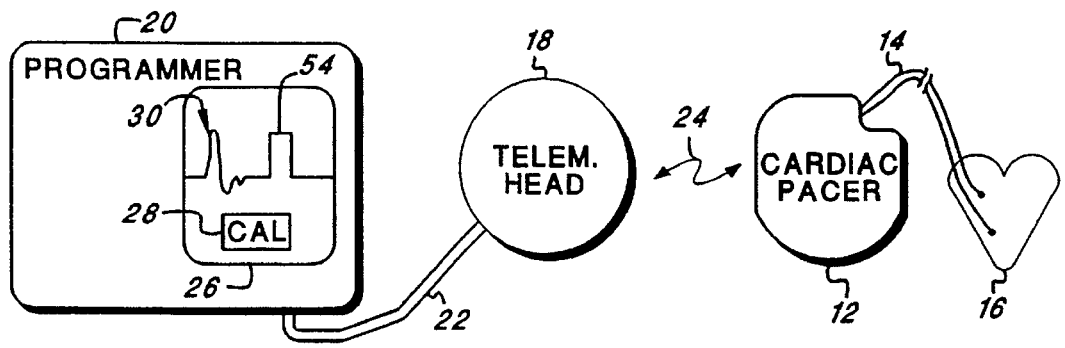
FIG. 1 shows a pacemaker/programmer system, with the pacemaker being coupled to a heart via pacing leads, and with the programmer and pacemaker being coupled to each other through electromagnetic telemetry signals.

Turning first to FIG. 1, there is shown a pacemaker programmer system made in accordance with the present invention. The system includes an implantable pacemaker 12 coupled to a heart 16 via pacing leads 14. For purposes of the present invention, the pacer 12 (note that the terms "pacemaker" and "pacer" are used as synonyms herein) may be any type of pacer or stimulator device, i.e., dual-chamber pacemaker, single-chamber pacemaker, implantable defibrillator, or other implantable device having internal or external signals transmitted thereto, therefrom, or therethrough, operating in any mode. All that is required is that the implantable device (pacer) 12 include conventional amplifier circuits that enable it to amplify the intracardiac electrogram (IEGM), or other signals to be telemetered to an external programmer, through the leads 14. Such leads 14, as is known in the art, may comprise either bipolar or unipolar leads, and may interface with the amplifier circuits of the pacemaker using various electrode configurations, including tip-to-ring, tip-to-case, and ring-to-case.

Once amplified within the pacemaker 12, the IEGM is converted to appropriate IEGM signals that are telemetered to a telemetry head 18 via a telecommunications link (represented by the wavy arrow 24). Other signals in addition to IEGM signals may also be telemetered from the pacer to the telemetry head 18, as is known in the art. The telemetry head 18 receives the telemetered signals and passes them to an external programmer 20 via a connecting cable 22. Once received at the programmer 20, the IEGM signals are appropriately processed and: (1) displayed on a display screen 26 of the programmer 20; (2) printed by a printer included as part of, or coupled to, the programmer 20; or (3) stored for subsequent retrieval and analysis.

The display of the IEGM signals on the screen 26 is typically presented as an x-y trace 30, divided into graticulations, or graticules, that shows the amplitude of the IEGM signals on one axis (e.g., the "y" or vertical axis) and time on the other axis (e.g., the "x" or horizontal axis). Hence, the trace 30 shows cardiac waveforms that appear similar to EKG traces obtained using skin electrodes and an external EKG machine.

It is noted that most programmers 20 further include a printer that allows the IEGM signals to be printed as a function of time. Such printing, when made, is thus very similar to the printed traces obtained from a conventional skin-electrode EKG machine.

Most of the circuits and components used within the cardiac pacer 12 and the external programmer 20 are of conventional design, and may be fabricated to operate as is known in the art. For example, representative pacemaker circuitry that may be used within the implantable pacemaker 12 is disclosed in U.S. Pat. Nos. 4,712,555; 4,788,980; 5,292,341; 5,309,919, and in U.S. patent application Ser. No. 08/225,226, filed Apr. 8, 1994, owned by the same entity as the present application. Representative circuitry for use within the external programmer is disclosed, e.g., in U.S. Pat. Nos. 4,791,936 and 4,809,697. The patents and application identified in this paragraph are incorporated herein by reference.

A key feature of the present invention, as explained more fully below, relates to the use of a calibrate button 28 (or other calibrate switch or selection means) located at the programmer 20. Such button or switch is used to verify or calibrate the amplitude of the IEGM signals received from the pacemaker. As such, the calibrate button 28 provides a viable technique for verifying the pacemaker/programmer system "gain", i.e., how much the IEGM is amplified or attenuated as it is passed from the pacemaker to the programmer.

Figure 2:
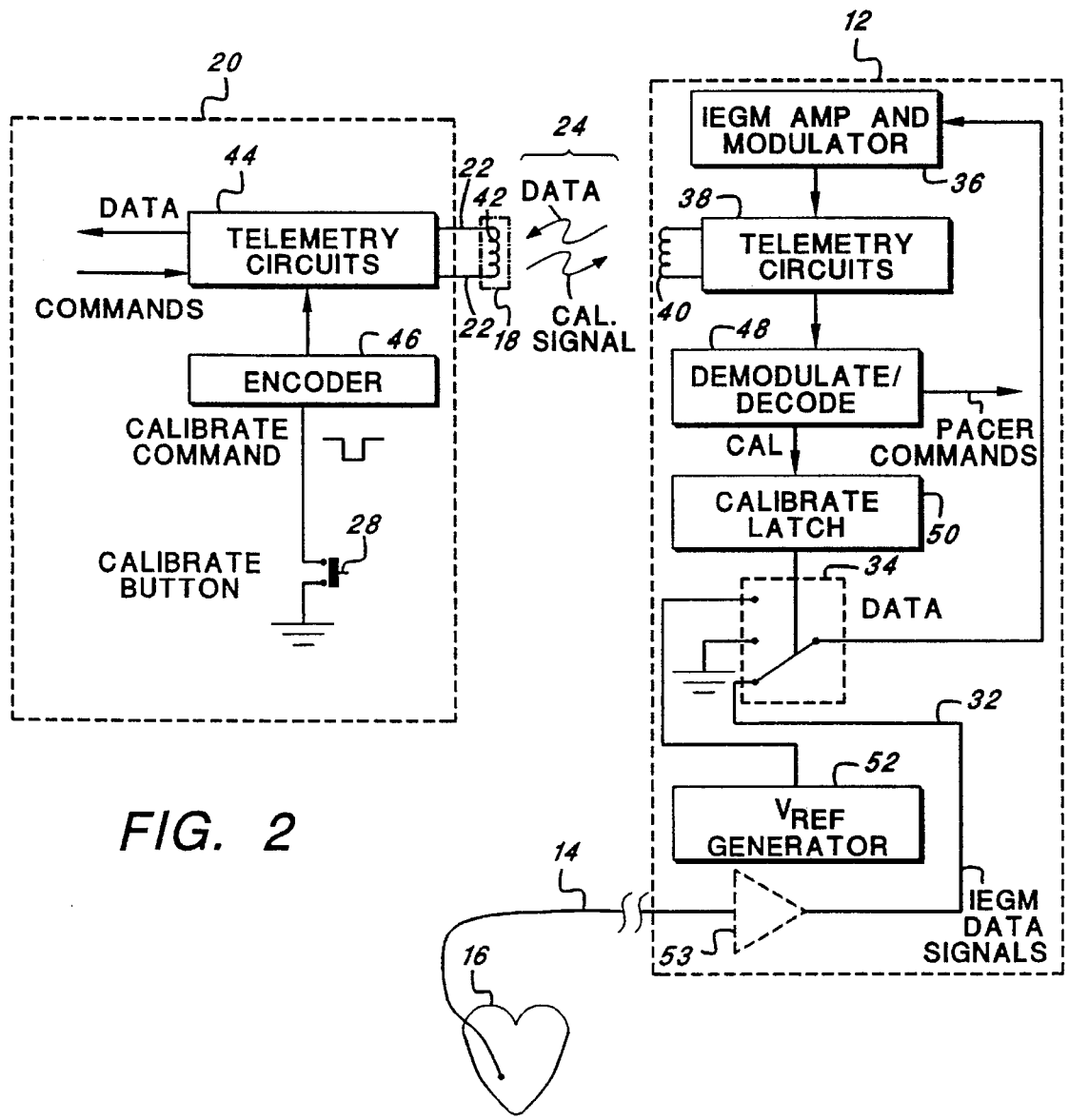
FIG. 2 shows a functional block diagram of the system of FIG. 1.

Turning to FIG. 2, a functional block diagram of the pacing system of FIG. 1 is shown. Only those components of the system that relate to the present invention are included in the block diagram. Hence, while there are many other functions performed by, and components or circuits included within, an implantable pacemaker and external programmer than are shown or illustrated in FIG. 2, such other functions, components and circuits are omitted from FIG. 2 for simplicity.

The IEGM is sensed through the leads 14 (coupled with the heart 16) through a conventional IEGM channel(s) included within the pacer 12. Such channel may include a well-characterized, broad-band pre-amplifier 53 that has a known fixed gain. (Note, such pre-amplifier 53, if used, is not the same as the atrial or ventricular sense amplifiers used to sense P-waves and R-waves.) The IEGM signals are monitored so that they may be telemetered to the external programmer 20. The circuitry that performs the IEGM signal amplification, filtering, and modulation is functionally depicted in FIG. 2 as the IEGM Amplifier and Modulator 36. In accordance with the present invention, during an appropriate telemetry mode, i.e., when the pacer 12 has been programmed to telemeter the IEGM to the programmer 20, the IEGM data signals, on signal line 32, are passed through a calibration selection switch 34 to the IEGM amplifier/modulator 36, and then to the telemetry circuits 38 of the implantable pacer. While only a single signal line 32 is shown in FIG. 2, it is to be understood that two signal lines are usually employed so that the IEGM data signals may be passed differentially through the switch 34 to the amplifier/modulator 36.

Typically, the communication link 24 between the pacer 12 and the programmer 20 is established through the use of a carrier signal that is inductively coupled between an implanted coil 40, coupled to the telemetry circuits 38, and an external coil 42 included within the telemetry head 18. Such inductive coupling occurs most efficiently when the telemetry head 18 is placed on or near the surface of the skin of the patient immediately over the area where the pacer 12 is implanted. The carrier signal is modulated with the IEGM data signals. The modulated carrier signal is received by appropriate telemetry circuits 44 within the programmer 20, and is demodulated in order to recover the IEGM data. Such data is then processed for display and or storage in conventional manner.

In a similar fashion, command signals may be sent from the external programmer 20 to the implanted pacer 12. That is, once the telecommunications link is established, it is possible to send data, e.g., command signals, from the programmer 20 to the implanted pacer 12, as well as receive data, e.g., IEGM data signals, sent from the pacer.

It should be pointed out that inductive coupling (which is a form of magnetic coupling) is not the only way to establish a telecommunicative link between the pacer and the external programmer. Any type of data link that permits coupling of signals between the implanted pacer and the external programmer may be used, including, but not limited to: rf coupling; optical coupling; acoustic coupling; magnetic coupling (which, in addition to inductive coupling, includes reflected impedance monitoring, control of magnetic reed switches, etc.); direct coupling; and the like. The type of data link between the pacer and the programmer is not critical to the present invention. All that matters is that whatever link is used, it allows data to be sent from the pacer to the programmer, as well as allows commands to be sent from the programmer to the pacer.

In accordance with the invention, the programmer 20 includes a calibrate button 28, or equivalent switch, that when activated generates a calibrate command signal. The calibrate command signal is then processed (e.g., encoded by an encoder circuit 46) so that it can be distinguished from the other types of command signals that may be generated by the programmer. The encoded calibrate command signal is then passed on to the programmer telemetry circuits 44 so that it can be communicated through the data link 24 to the pacer 12.

At the pacer 12, the calibrate command signal is processed like all other commands received from the programmer. That is, it is recovered through demodulation, and then identified through decoding (using, e.g., conventional demodulation/decoding circuitry 48), to generate a calibrate command signal within the pacer. The calibrate command signal received at the pacer is identified as "CAL" in FIG. 2. (In practice, as described more fully below in connection with FIGS. 4A, 4B and 4C, such CAL signal may actually comprise a set of control signals that includes, in addition to the CAL signal, an IEGM SEL signal, and a ZERO signal, referred to collectively as the CAL signals.) Once thus generated within the pacer, the CAL signals operate a calibration latch 50, or equivalent device or function, to control the calibrate switch 34. When the CAL signals have been received, the switch 34 thus inserts one or more precision reference voltages into the data stream being telemetered to the programmer 20. Such precision reference voltages include, e.g., a zero voltage reference, $V_{ZERO}$, and a reference voltage, $V_{REF}$. In some instances, the CAL signal operates to momentarily replace the IEGM data signals with a sequence of the reference signals comprising first the $V_{ZERO}$ signal, then the $V_{REF}$ signal, and then the $V_{ZERO}$ signal again. In other instances, the CAL signals operate to replace the IEGM data signals permanently (i.e., until another command is received to override the ZERO and CAL signals). In still other instances, the CAL signals operate to momentarily superimpose the reference voltage, $V_{REF}$, onto the IEGM data signals. The zero voltage reference signal $V_{ZERO}$ is simply the zero (or ground) reference potential of the pacemaker. The precision $V_{REF}$ signal is generated by a $V_{REF}$ generator circuit 52 included within the pacer. The $V_{REF}$ signal may thus be telemetered to the programmer for a time, e.g., for as long as the calibrate button is activated at the programmer, preceded and followed by, e.g., 5 ms of the $V_{ZERO}$ signal; or the $V_{ZERO}$-$V_{REF}$-$V_{ZERO}$ sequence may be telemetered to the programmer for a fixed duration, e.g., 5 ms of $V_{ZERO}$, 10–20 milliseconds (ms) of $V_{REF}$, followed by 5 ms of $V_{ZERO}$, in lieu of the IEGM data signals. Alternatively, the $V_{REF}$ signal may be added to the IEGM data signals being telemetered to the programmer for a time, e.g., for as long as the calibrate button is activated, or for a fixed duration, e.g., 10–20 ms.

When the $V_{ZERO}$ and $V_{REF}$ signals are telemetered to the programmer in lieu of the IEGM data signals, they are received and processed at the programmer 20 just as though they were IEGM data signals. Hence, when the IEGM is displayed at the programmer, and assuming that the calibrate button 28 has been activated, the display of the IEGM on the display screen 26 of the programmer 20 (or as printed by the printer of the programmer) includes a pulse 54 or level representing the magnitude of the $V_{ZERO}$-to-$V_{REF}$-to-$V_{ZERO}$ signal sequence as the $V_{ZERO}$-$V_{REF}$-$V_{ZERO}$ signal sequence is received and processed by the programmer 20. Such a pulse is shown below in FIG. 6A. Because the magnitude of $V_{REF}$ is known, the representation of $V_{REF}$ at the programmer thus serves as a means of calibrating or verifying the amplitude of the IEGM signals as such signals are received at the programmer.

When the $V_{REF}$ signal is combined with the IEGM data signals, e.g., added to the IEGM data signals, such signals are likewise received and processed at the programmer 20 in the same manner as are the IEGM data signals. Hence, when a display of the IEGM is presented on the display screen 26 of the programmer 20 (or is printed by the printer of the programmer), a pulse 59 is superimposed within the display having a offset magnitude of $V_{REF}$, which offset magnitude is probably best seen at the leading edge or the trailing edge of the pulse 59, as illustrated below in FIG. 6B.

Figure 3:
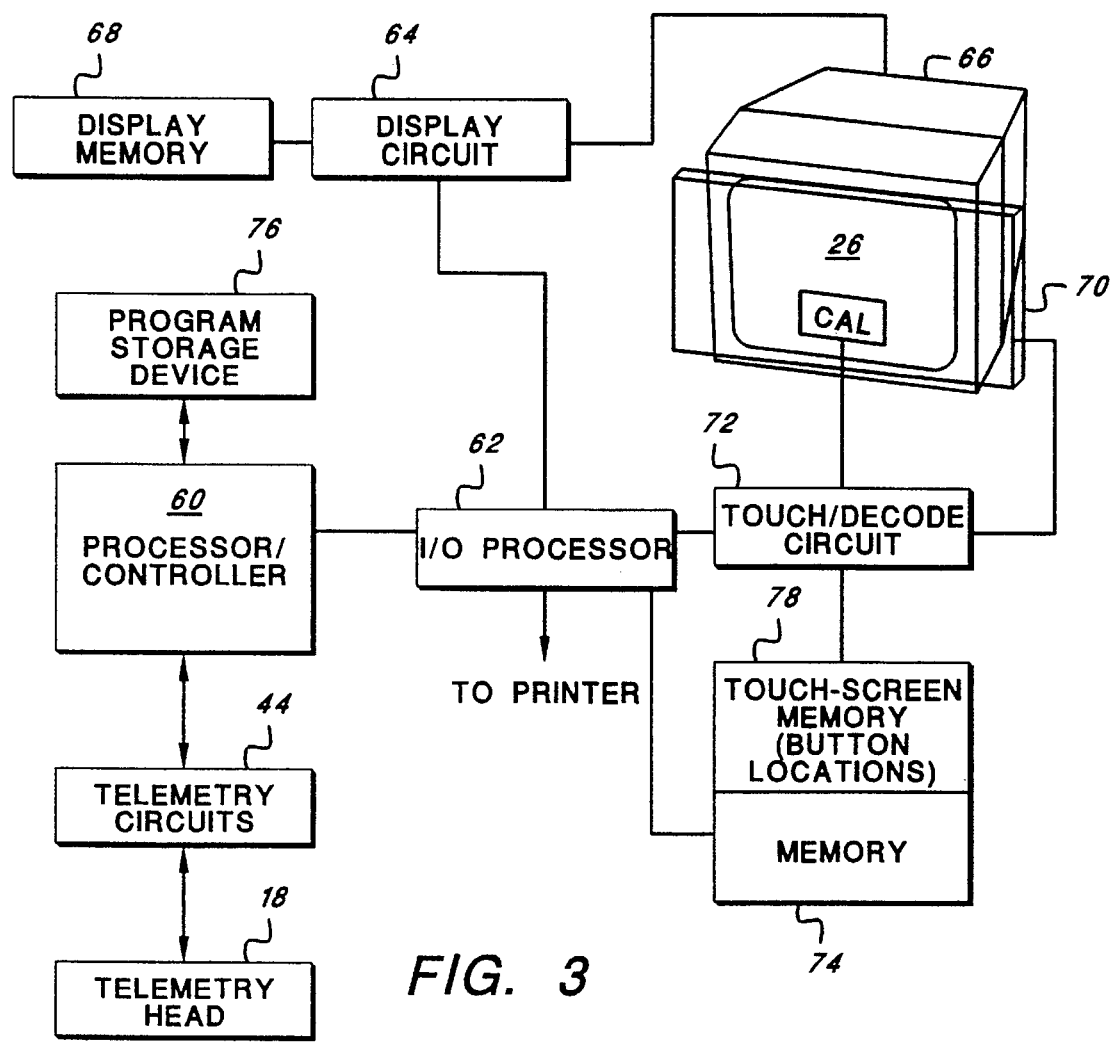
FIG. 3 is a block diagram of the external programmer.

Turning next to FIG. 3, a simplified block diagram of the external programmer 20 is shown. The detailed operation of the programmer 20 is the same as is known in the art, see, e.g., U.S. Pat. No. 4,809,697. Essentially, the programmer is controlled by a microprocessor 60, also referred to as a main processor, or processor/controller. A program storage device 76, e.g., a ROM cartridge, a floppy diskette, a hard disk, etc., contains an operating program that controls the main processor 60 in a desired manner. Additional memory circuits 74 provide storage of data and other parameters not directly associated with the operating program. An input/output (I/O) processor 62 facilitates the transmission of data and commands to and from the main processor 60. In order for the programmer to generate a desired display, the I/O processor 62 interfaces with a display circuit 64. The display circuit 64 is connected to a CRT (or other type) display 66 and a display memory 68. The display circuit 64, display 66, and display memory 68 operate in conventional manner in order to display desired signals and/or other information on the screen 26.

In a preferred embodiment, the calibrate button 28 is provided by use of a transparent touch-sensitive screen 70 that overlays the screen 26. One or more buttons or blocks are displayed on the CRT screen at known locations. E.g., the calibrate button 28 is displayed on the screen at known coordinates. Because the touch screen 70 is transparent, the button 28 is readily visible therethrough. The touch-sensitive screen 70 is connected to a touch/decode map circuitry 72, which in turn is coupled to a touch-screen memory 78. When a user touches the screen 70, the touch/decode map circuitry determines the relative coordinates at which the touching occurs. If the coordinates match those of a specified button stored in the touch screen memory 78, e.g., those of the displayed calibrate button 28, then the touch screen map circuitry determines that the calibrate button has been activated, and generates an appropriate calibrate command signal.

Touch-sensitive screens are commercially available components, and the use and operation of such touch-sensitive screens in combination with a display 66 to function as an input device for a processor or computer are known in the art.

The calibrate button 28 may, of course, be realized using other manual activation devices or switches other than a touch-sensitive screen. A conventional push button switch, for example, could be mounted in the front panel of the programmer 20. For safety and ease-of-use considerations, however, it is generally preferred that the programmer, which is used by doctors and other medical personnel in an operating room, not use any switches or buttons beyond those displayed on the screen. Further, it is not necessary that the calibrate button 28 be of the type that is always manually activated. It is also possible for the processor 60, as part of its operating program, to regularly generate the calibrate command signal whenever IEGM telemetry data is being received from the pacer, thereby effectively providing software activation of the calibrate button. Further, the processor 60 may periodically generate the calibrate command signal whenever IEGM telemetry data is being received from the pacer, thereby performing the calibration function on a periodic basis during telemetry. Those of skill in the art would thus not be limited to using touch-screen technology, but could readily fashion an appropriate means for generating the calibrate command signal as a function of their particular needs for a given pacing/monitoring application.

Figure 4A:
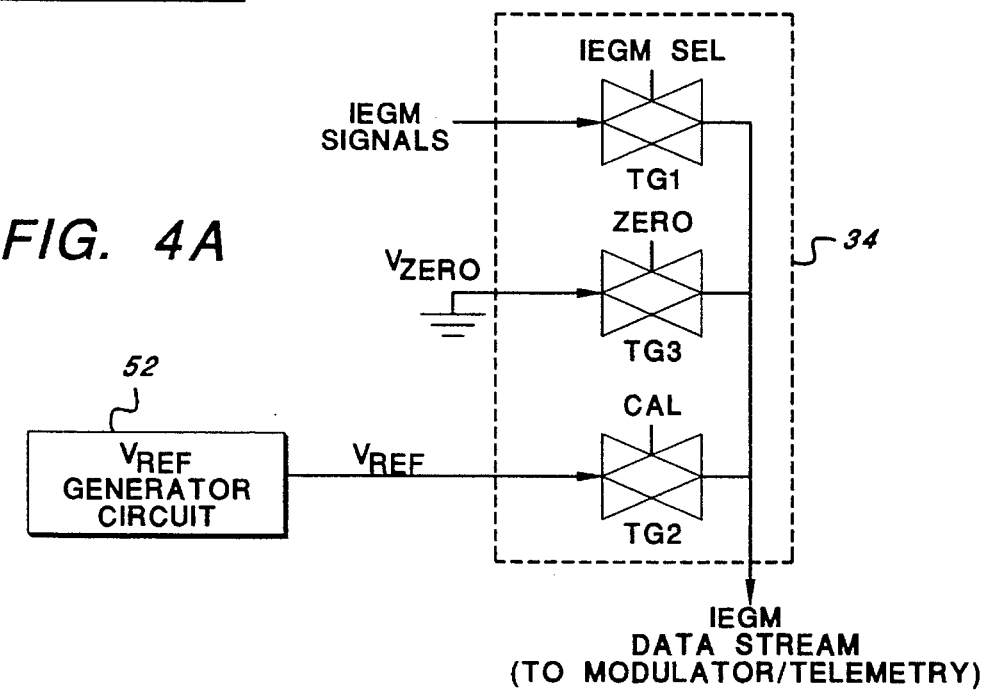

FIG. 4A shows a schematic block diagram of one configuration of the precision reference voltage circuit 52 and calibration selection switch 34 used within the pacemaker 12. The switch 34 is realized from a first transmission gate TG1, a second transmission gate TG2, and a third transmission gate TG3. The input terminal of the first transmission gate TG1 is connected to the IEGM signals. The input terminal of the second transmission gate TG2 is connected to receive the precision reference voltage $V_{REF}$ from the $V_{REF}$ generator circuit 52. The input terminal of the third transmission gate TG3 is connected to ground potential, which potential serves as the reference $V_{ZERO}$. The output terminals of all three transmission gates are connected together and directed to the amplifier/modulator/telemetry circuits 36, 38 (FIG. 2). The control lines of each transmission gate are connected to set of CAL control signals generated by the demodulator/decoder circuit 48 (CAL, IEGM SEL, and ZERO). complimentary signals of the calibrate command signal When a transmission gate is turned ON, it passes an analog signal therethrough, just as does a closed switch. When a transmission gate is turned OFF, it blocks the passage of an analog signal therethrough, just as does an open switch.

FIG. 4B shows an alternate configuration of the precision reference voltage circuit 52 and calibration selection switch 34'. In the configuration shown in FIG. 4B, the transmission gate TG2 selectively adds the precision reference voltage $V_{REF}$ to the IEGM signals through a combining circuit element 55. The circuit element 55 combines (adds) the signals applied to its inputs, and may be realized, e.g., with an operational amplifier. When the CAL signal is present, the transmission gate TG2 is turned on, thereby sending the $V_{REF}$ signal through the gate TG2 to be added to the IEGM data stream. When the CAL signal is not present, the transmission gate TG2 is turned off, thereby allowing only IEGM signals to be sent through the combiner 55 as the IEGM data.

Figure 4C:
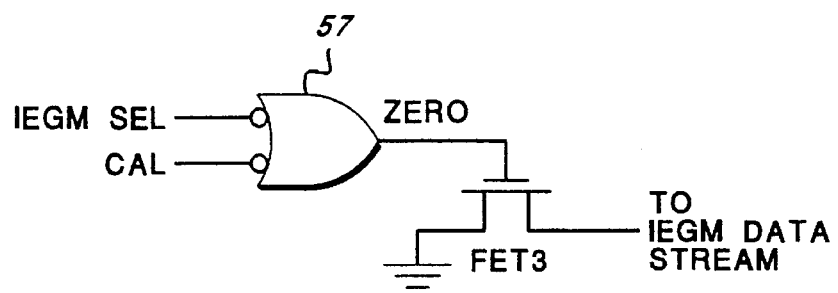
FIG. 4C shows one embodiment of the transmission gate TG3 of FIG. 4-1.

FIG. 4C shows one way in which the transmission gate TG3 of FIG. 4A may be realized. A single field-effect transistor switch FET3 has its source terminal S grounded (which serves as the $V_{ZERO}$ input), and its drain terminal D (which serves as its output) is coupled to the IEGM data stream. Its gate terminal G has the ZERO control signal applied thereto, so that when the ZERO control signal is high (asserted), FET3 is turned on, connecting its source terminal to its drain terminal, and when the ZERO control signal is low, FET3 is turned off, disconnecting the source from the drain. The ZERO control signal may be generated using logic gate circuitry 57 that provides an inverted-input-OR function. The IEGM SEL signal is applied to one input of gate 57, and the CAL signal is applied to the other input of gate 57. Only when both the IEGM SEL or CAL signals are not present, is the ZERO signal asserted.

Figure 5C:
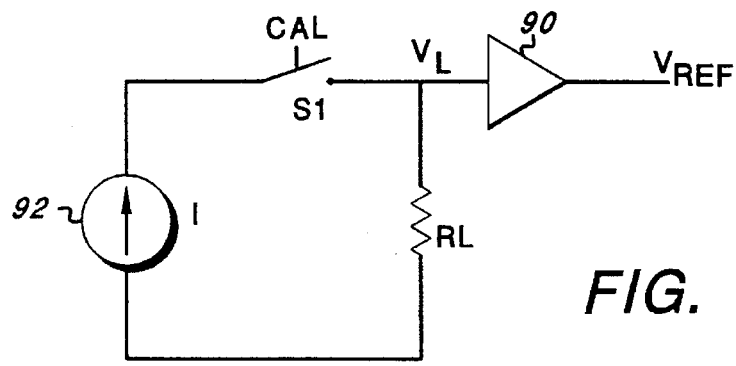

FIGS. 5A, 5B and 5C illustrate representative embodiments of the precision reference voltage circuit 52 that may be used with the present invention. It is noted that the circuits shown in FIGS. 5A, 5B and 5C, as well as the circuits shown in FIGS. 4A, 4B and 4C, are not meant to be exhaustive.

In FIG. 5A, a reference voltage circuit is shown that generates a voltage pulse having a precision amplitude $V_{REF}$. The circuit includes a zener diode 82, a bandgap circuit, or equivalent component that generates a precise reference voltage when an electrical current flows therethrough, connected, in the case of the zener diode, in series with a resistor R1. The resistor is connected to the pacer battery V1 and filter capacitor C1 through a transmission gate 84. The transmission gate 84 is controlled by a short single-pulse generator 86, which single-pulse generator is triggered by receipt of the CAL signal. A companion single-pulse generator 87 produces a longer single-pulse upon receipt of the CAL signal. The short single-pulse generator 86 generates a short pulse, e.g., 0.1 msec., which turns on transmission gates 84 and 103. With transmission gate 84 turned on, a short pulse, having a magnitude of about 0.1 msec., is passed through the ON transmission gate 103 to the storage capacitor C2, thereby charging capacitor C2 to a value equal to $V_{REF}$. A unity gain buffer amplifier 101 applies the voltage stored on capacitor C2 to the input of transmission gate 102. Transmission gate 102 is turned on for the duration of the longer pulse, generated by pulse generator 87. Hence, for the duration of the longer pulse, the reference voltage $V_{REF}$ appears at the output of the $V_{REF}$ generator circuit 52.

The single-pulse generators 86 and 87 may be of conventional design, and comprise circuits that generate respective single pulses upon being triggered by the CAL signal. A one-shot multivibrator circuit of conventional design could be used for this purpose. Alternatively, a single-pulse generator circuit can be made with logic gates and latch circuits, as is known in the art. The long pulse generated by the single-pulse generator circuit 87 may be of any width, but is preferably at least 10–20 milliseconds, thereby giving the pulse enough width to make it readily discernable on the display 26 of the programmer 20.

In operation, receipt of the CAL signal triggers the one-shot pulse generators 86 and 87 causing them to generate pulses of fixed widths. The transmission gate 84 is then turned ON for the duration of the short pulse generated by the generator 86, thereby enabling a current to flow from the battery V1 and shunt capacitor C1 through the series connection of the resistor R1 and the zener diode 82. The value of the resistor R1 is selected to set the magnitude of the zener current (the current flowing through the zener diode) at a desired value. The current flow through the zener diode 82 causes a fixed, known voltage, $V_{REF}$, to appear across the diode 82 for so long as the current flows through the diode. Hence, a voltage pulse, having a duration equal to the duration of the pulse generated by the pulse generator 86, and having an amplitude equal to $V_{REF}$, is generated upon receipt of the CAL signal. Such voltage pulse is then transferred to and stored on capacitor C2 through transmission gate 103, buffered by amplifier 101, and inserted via transmission gate 102 (turned on for the duration of the long pulse) into the data stream (in lieu of or in addition to IEGM signals) being telemetered to the programmer 20.

It is noted that the zener diode is pulsed as described above in order to conserve power within the pacer 12. When the $V_{REF}$ pulse is not being generated, there is very little power consumed by the $V_{REF}$ generator circuit shown in FIG. 5A.

It is also noted that numerous semiconductor devices could be used in lieu of the zener diode 82 shown in FIG. 5A. Most semiconductor devices exhibit a known current-voltage relationship, so that for a range of current flowing therethrough, a known voltage is present across the device. Hence, for purposes of the present invention, the circuit of FIG. 5A could use many and varied components.

In FIG. 5B, the precision 2.800 volts of a lithium-iodide battery is "floated" onto an isolated storage capacitor C3 by the select closing and opening of field effect transistor (FET) FET1. For purposes of FIG. 5B, FET1 closes when its gate voltage goes low, which due to inverter gate 103 happens when the REF GEN signal is high. Thus, in the absence of the REF GEN signal (REF GEN signal low), i.e., when the calibrate function of the invention has not been selected, FET1 is turned on, and capacitor C3 is charged to the loaded output voltage of the lithium iodide battery. During this non-calibrate time, a sample and hold circuit 105 is open circuited (not powered) because FET2, held off (open) by the low REF GEN signal, keeps power from being applied to its power input. When the REF GEN signal goes high, the gate of FET1 goes low, causing capacitor C3 to be isolated from the battery. However, the lithium iodide battery voltage remains stored on the capacitor C3 and is applied to the sample input of the sample and hold circuit 105. At this same time, FET2 is turned on, applying the unloaded battery voltage to the sample and hold circuit 105. The circuit 105 thus samples the unloaded battery voltage when the REF GEN signal is high. The circuit 105 further includes a conventional divide circuit that divides the sampled voltage down by a prescribed factor, e.g., ½, to produce the precision reference voltage, $V_{REF}$. Note that the REF GEN signal is typically a short pulse that is generated coincident with receipt of the CAL signal.

FIG. 5C illustrates yet another embodiment of the $V_{REF}$ generator circuit 52. The embodiment of FIG. 5C switchably connects a precision current source 92 to a load $R_L$ through a switch S1. The load $R_L$ has a fixed resistance, so when a fixed current I flows therethrough, a known voltage $V_L$ is developed. A buffer amplifier 90, having a fixed gain, then amplifies the voltage $V_L$ as required to produce the reference voltage $V_{REF}$. The switch S1 may be realized using a MOSFET transistor that is turned OFF or ON by the CAL signal. Alternatively, the switch S1 may be a conventional transmission gate. The current source 92 may be of conventional design using available transistors and other devices on the integrated circuit chip on which the other pacing circuits are made.

When the $V_{REF}$ signal is received at the programmer, it is processed the same as the IEGM data. Thus, as it is sent to the programmer, and as it is processed within the processing circuits of the programmer, it is attenuated and amplified, and otherwise processed, just like the IEGM data signals. Advantageously, because the $V_{REF}$ signal has a known amplitude at the beginning of its transmission to the programmer, such known amplitude can be used to calibrate the display (or other analysis) of the IEGM data signals. This is true regardless of whether the IEGM signals are displayed in real time, or stored for subsequent display and analysis. Note, that if stored rather than displayed, the $V_{REF}$ signal is stored along with the IEGM data signals, so that when the stored IEGM data is later retrieved and displayed or analyzed, the $V_{REF}$ signal remains interleaved with the IEGM data, and thus still provides a means for calibrating and/or verifying the IEGM data.

Figure 6B:
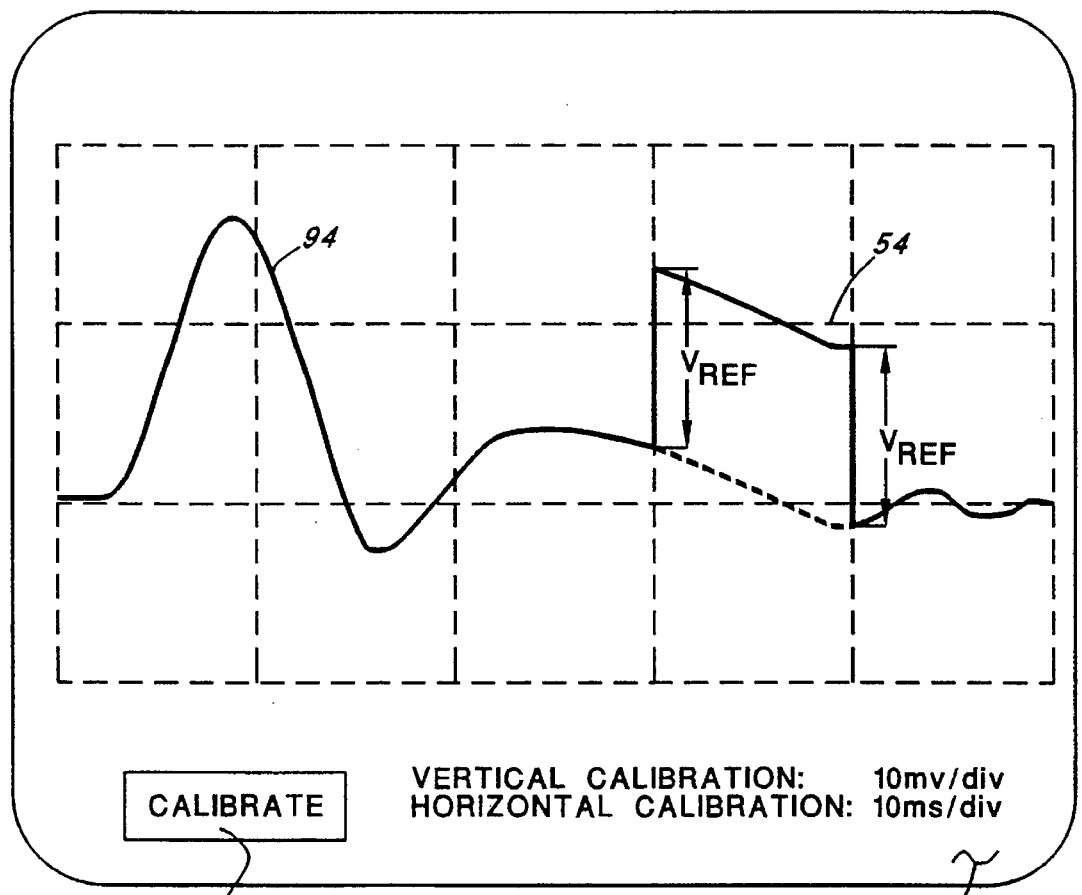
FIGS. 6A and 6B show respective representative displays of the IEGM and a calibrate signal on a screen of the external programmer for alternative embodiments of the invention, and further illustrate how the grid of such display may be used to determine the amplitude of the IEGM signals from the level of the calibrate signal also displayed.
Figure 6A:
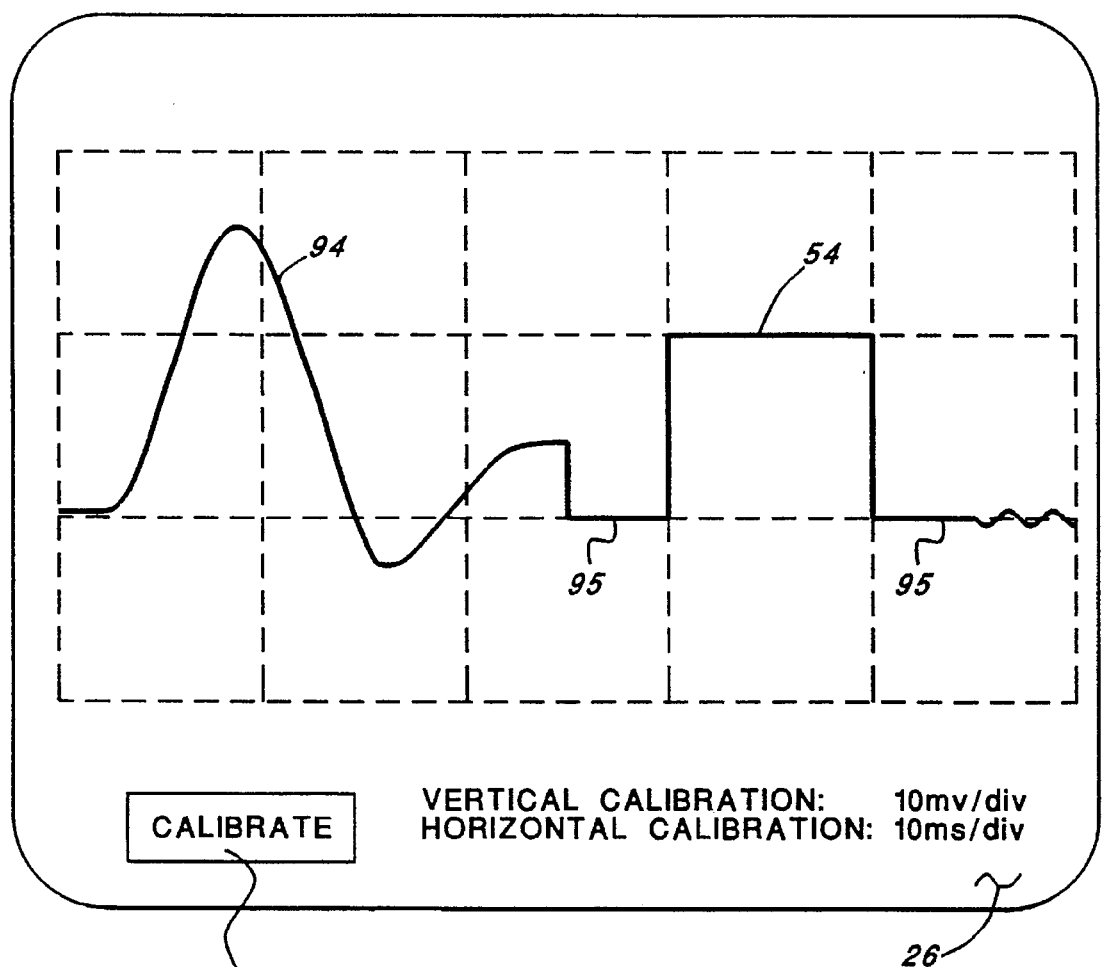

FIG. 6A depicts a representative display of the IEGM and a calibrate signal pulse 54 as they appear on the screen 26 of the external programmer. Note that the pulse 54 is preceded and followed by a short $V_{ZERO}$ level. Hence, the display depicted in FIG. 6A is for a calibration pulse sequence that has been inserted into the IEGM data stream within the pacemaker, in place of the IEGM data, e.g., using a circuit such as that shown in FIG. 4A above. A preferred display screen 26 employs a grid system (shown by dotted lines in FIG. 6A) that aids in comparing the amplitude and/or pulse width of the $V_{REF}$ pulse to the remaining IEGM display. For example, in FIG. 6A, the grid system is adjusted as needed so that the calibration $V_{REF}$ pulse 54 has an amplitude equal to one division. This one division is then relatable to an absolute volts per division based on the known amplitude of the $V_{REF}$ pulse. As seen in FIG. 6A, an adjacent R-wave pulse may have an amplitude of 1.5 divisions, meaning that the R-wave 94 has an amplitude that is about 1.5 times that of the $V_{REF}$ pulse 54, i.e., 15 millivolts for the waveform represented in FIG. 6A. Such data can be recorded for a given patient, e.g., by simply printing the IEGM display. Then, during a subsequent visit of the patient, another IEGM signal trace (IEGM data) may be recorded in a similar manner. The two recordings can then be compared to see if there has been any significant change in the magnitude of the recorded IEGM. Such comparison will thus indicate whether the actual patient signal amplitude(s) has (have) changed significantly since the patient's last visit.

FIG. 6B is the same as FIG. 6A, except that the calibration pulse 59 has been added to the IEGM data stream within the pacemaker, e.g., using a circuit such as that shown in FIG. 4B above. As seen in FIG. 6B, the $V_{REF}$ pulse 59 does not have a "flat" level top. However, the precision $V_{REF}$ value is still just as evident at the leading edge and trailing edge of the pulse.

As described above, it is thus seen that the invention provides an IEGM calibration system that allows the system "gain" of a pacemaker/programmer system to be verified and/or adjusted by generating and injecting a calibrated voltage pulse or level into the IEGM data that is telemetered from an implanted pacemaker to an external programmer upon command from the external programmer. Advantageously, such system allows the IEGM sensed by the pacemaker to be displayed or printed, and even permits the absolute volts per division of such display or print to be determined relative to a known magnitude of the calibrated voltage pulse or level.

While the invention herein disclosed has been described by means of specific embodiments and applications thereof, numerous modifications and variations could be made thereto by those skilled in the art without departing from the scope of the invention set forth in the claims.

What is claimed is:

1. A cardiac pacemaker system comprising:

an implanted pacemaker, the pacemaker having means for sensing intracardiac electrogram (IEGM) signals and means for telemetering such IEGM signals to a remote receiver;

an external programmer in telemetered contact with the implanted pacemaker, the programmer having:
receiver means for receiving the IEGM signals telemetered from the implanted pacemaker,
processing means for processing the received IEGM signals for display, and
display means for displaying the processed IEGM signals as a function of a selected time base;

the implanted pacemaker further having:
means for generating a plurality of voltage reference signals, each having a fixed magnitude,
means responsive to a calibrate signal for inserting a prescribed sequence of the plurality of voltage reference signals in a data stream of the sensed IEGM signals telemetered to the programmer, and
implanted receiver means for receiving control signals from the external programmer; and the external programmer further having:
    means for selectively generating the calibrate signal, and
    means for coupling the calibrate signal to the implanted receiver, thereby causing the prescribed sequence of the plurality of voltage reference signals to be included in the data stream received from the implanted pacemaker;
    whereby the sequence of voltage reference signals, when selectively inserted into the data stream of the sensed IEGM signals, becomes part of the IEGM signals displayed by the display means of the external programmer, and
    whereby the fixed magnitude of the plurality of voltage reference signals thus displayed can be used to calibrate the display of the IEGM.

2. The pacemaker system of claim 1, wherein the means for selectively generating the calibrate signal in the external programmer includes:
    switch means for manually activating a calibrate function; and
    command signal generating means responsive to activation of the switch means for generating the calibrate signal.

3. The pacemaker system of claim 2, wherein the switch means includes:
    a transparent touch sensitive membrane placed over a display screen of the external programmer;
    means for displaying a calibrate button on the display screen; and
    means responsive to touching the membrane at a location that is over the displayed calibrate button on the display screen for generating the calibrate signal.

4. The pacemaker system of claim 1, wherein the means for selectively generating the calibrate signal in the external programmer comprises means for automatically generating the calibrate signal whenever the data stream of IEGM signals is being received from the implanted pacemaker.

5. The pacemaker system of claim 1, wherein the means for selectively generating the calibrate signal in the external programmer comprises means for periodically generating the calibrate signal whenever the data stream of IEGM signals is being received from the implanted pacemaker.

6. The pacemaker system of claim 1, wherein the means for generating the plurality of voltage reference signals comprises means for generating a reference voltage pulse having a fixed amplitude that is inserted into the data stream of the sensed IEGM signals.

7. The pacemaker system of claim 6, wherein the means for generating the plurality of voltage reference signals comprises a zero reference voltage $V_{ZERO}$, and a reference voltage, $V_{REF}$, and means for generating a $V_{ZERO}$-$V_{REF}$-$V_{ZERO}$ sequence that is interleaved with the data stream of the sensed IEGM signals.

8. The pacemaker system of claim 7, wherein the $V_{ZERO}$-$V_{REF}$-$V_{ZERO}$ sequence comprises no more than about 5 ms of a $V_{ZERO}$ signal, followed by no more than about 20 ms of a $V_{REF}$ signal, followed by no more than about 5 ms of the $V_{ZERO}$ signal.

9. The pacemaker system of claim 1, wherein the display means of the external programmer comprises an electronic display screen upon which the processed IEGM signals and the plurality of reference voltage signals are displayed.

10. The pacemaker system of claim 1, wherein the display means of the external programmer comprises a printer that prints the processed IEGM signals and the plurality of reference voltage signals in a tangible medium.

11. An IEGM calibration system comprising an implantable pacemaker and an external programmer, the implantable pacemaker comprising:
    a receiver that receives control signals from a remote transmitter;
    sensing means for sensing intracardiac electrogram (IEGM) signals;
    telemetry means for telemetering the IEGM signals to a remote receiver;
    a voltage source that generates a plurality of fixed-level precision reference voltages; and
    a switching circuit, responsive to a calibration control signal, that switches a prescribed sequence of the plurality of fixed-level precision reference voltages into a data stream of the sensed IEGM signals that are telemetered to the remote receiver;
    the external programmer comprising:
    the remote receiver,
    the remote transmitter,
    processing means for processing the received IEGM signals for display,
    display means for displaying the processed IEGM signals as a function of a selected time base,
    means for selectively generating the calibration control signal and transmitting it to the implanted receiver within the pacemaker through the remote transmitter, thereby causing the prescribed sequence of the plurality of fixed-level precision reference voltages to be interleaved with the IEGM signals telemetered to the programmer,
    whereby the precision reference voltage may be selectively included within the IEGM signals that are received by the remote receiver and processed for calibration purposes by the processing means of the external programmer.

12. The IEGM calibration system of claim 11, wherein the external programmer further includes memory means for storing the processed IEGM signals and plurality of fixed-level precision reference voltages for later display and analysis.

13. The IEGM calibration system of claim 11, wherein the switching circuit of the implanted pacemaker includes means for inserting the plurality of fixed-level precision reference voltages into the data stream of IEGM signals as a sequence that defines a pulse having a fixed amplitude.

14. The IEGM calibration system of claim 11, wherein the switching circuit of the implanted pacemaker has at least first, second, third and fourth states, a first state during which a first of the plurality of fixed-level precision reference voltages is momentarily inserted into the data stream, a second state during which a second of the plurality of fixed-level precision reference voltages is inserted into the data stream, a third state during which the first of the plurality of fixed-level precision reference voltages is again momentarily inserted into the data stream, and a fourth state during which the IEGM data signals are inserted into the data stream, and further including means responsive to the calibration control signal for controlling the switching circuit so that it assumes in sequence its first, second and third states whenever the calibration control signal is received by the implanted receiver of the pacemaker, and so that it assumes its fourth state whenever the calibration control signal is not received by the implanted receiver, whereby the plurality of fixed-level precision reference voltages appear as a fixed voltage level relative to the first fixed-level reference voltage in the data stream for so long as the calibration control signal is received.

15. The IEGM calibration system of claim 11, wherein the voltage source of the implantable pacemaker includes:

means for generating a calibrate pulse of a fixed duration in response to receipt of the calibration control signal; and means for energizing the voltage source for the duration of the calibrate pulse, whereby the voltage reference source generates the plurality of fixed-level precision reference voltages only for the duration of the calibrate pulse.

16. A method of verifying the system gain of a pacing system, the pacing system comprising an implantable pacemaker and an external programmer, implantable pacemaker having means for sensing IEGM signals, means for transmitting the IEGM signals to an external receiver, and means for receiving command signals from a remote transmitter, the method comprising:

(a) establishing a data link between the pacemaker and the external programmer, the external programmer including the remote receiver and the remote transmitter;

(b) transmitting the IEGM signals from the pacemaker to the external programmer;

(c) receiving the IEGM signals at the external programmer;

(d) generating a calibrate command signal at the external programmer and sending the calibrate command signal to the pacemaker through the established data link;

(e) receiving the calibrate command signal within the pacemaker and, in response thereto, generating a plurality of fixed-level reference signals that are interleaved with the IEGM signals being telemetered to the external programmer, the plurality of fixed-level reference signals each having a known magnitude;

(f) receiving the plurality of fixed-level reference signals at the external programmer interleaved with the IEGM signals; and (g) processing the received IEGM signals with the received fixed-level reference signals in order to verify the system gain of the pacing system, the system gain being manifest from the magnitude of the received IEGM signals as scaled to the known magnitude of the received fixed-level reference signals.

17. The method of claim 16, further including storing the IEGM signals and plurality of fixed-level reference signals at the external programmer.

18. The method of claim 16, further including displaying the IEGM signals and plurality of fixed-level reference signals on a display device coupled to the external programmer.

19. The method of claim 18, wherein displaying the IEGM signals and reference signal on the display device comprises adding the reference signal to the IEGM signals for a prescribed period of time to produce a summed signal, and displaying such summed signal on the display device.

20. A cardiac pacemaker system comprising:

an implanted pacemaker, the pacemaker having means for sensing intracardiac electrogram (IEGM) signals and means for telemetering such IEGM signals to a remote receiver;

an external programmer in telemetered contact with the implanted pacemaker, the programmer having:
receiver means for receiving the IEGM signals telemetered from the implanted pacemaker,
processing means for processing the received IEGM signals for display, and
display means for displaying the processed IEGM signals as a function of a selected time base;

the implanted pacemaker further having:
means for generating a reference voltage signal having a selectable fixed amplitude,
means for adding the reference voltage level to the IEGM data signals during a portion of the data stream,
means responsive to a calibrate signal for inserting the reference voltage signal in a data stream of the sensed IEGM signals telemetered to the programmer, and
implanted receiver means for receiving control signals from the external programmer; and the external programmer further having:
means for selectively generating the calibrate signal, and
means for coupling the calibrate signal to the implanted receiver, thereby causing the reference voltage signal to be included in the data stream received from the implanted pacemaker;

whereby the reference voltage signal, when selectively inserted into the data stream of the sensed IEGM signals, becomes part of the IEGM signals displayed by the display means of the external programmer, and whereby the fixed magnitude of the reference voltage signal thus displayed can be used to calibrate the display of the IEGM.

21. A method of verifying the system gain of a pacing system, the pacing system comprising an implantable pacemaker and an external programmer, implantable pacemaker having means for sensing IEGM signals, means for transmitting the IEGM signals to an external receiver, and means for receiving command signals from a remote transmitter, the method comprising:

(a) establishing a data link between the pacemaker and the external programmer, the external programmer including the remote receiver and the remote transmitter;

(b) transmitting the IEGM signals from the pacemaker to the external programmer;

(c) receiving the IEGM signals at the external programmer;

(d) generating a calibrate command signal at the external programmer and sending the calibrate command signal to the pacemaker through the established data link;

(e) receiving the calibrate command signal within the pacemaker and, in response thereto, generating a reference signal that is included within the IEGM signals being telemetered to the external programmer, the reference signal having a known magnitude;

(f) receiving the reference signal at the external programmer with the IEGM signals;

(g) adding the reference signal to the IEGM signals for a prescribed period of time to produce a summed signal, and displaying such summed signal on a display device coupled to the external programmer; and (h) processing the received IEGM signals with the received reference signal in order to verify the system gain of the pacing system, the system gain being manifest from the magnitude of the received IEGM signals as scaled to the known magnitude of the received reference signal.

22. An implantable pacemaker comprising:

means for sensing intracardiac electrogram (IEGM) signals;

means for telemetering the IEGM signals to a remote receiver;

a voltage source that provides a first reference voltage having a fixed magnitude;

means for receiving a calibrate signal; and switch means responsive to receipt of the calibrate signal for adding the first reference voltage to the IEGM signals telemetered to the remote receiver for a prescribed time period;

the fixed magnitude of the first reference voltage thereby providing a way to calibrate the magnitude of the IEGM signals.

23. The implantable pacemaker of claim 22, wherein the voltage source additionally provides a second reference voltage, and wherein the switch means is for further adding the second reference voltage to the IEGM signals telemetered to the remote receiver.

24. The implantable pacemaker of claim 23, wherein the switch means adds the first and second reference voltages to the IEGM signals telemetered to the remote receiver in a prescribed sequence.

25. The implantable pacemaker of claim 24, wherein the prescribed sequence comprises the second reference voltage for no more than about 5 ms, followed by the first reference voltage for no more than about 20 ms, followed by the second reference voltage for no more than about 5 ms.

\* \* \* \* \*